United States Patent
Daidoji et al.

(10) Patent No.: US 9,814,375 B2
(45) Date of Patent: Nov. 14, 2017

(54) LIGHT SOURCE DEVICE AND SUBJECT OBSERVATION APPARATUS AS WELL AS LIGHT SOURCE CONTROL METHOD

(71) Applicant: OLYMPUS CORPORATION, Tokyo (JP)

(72) Inventors: Bakusui Daidoji, Hachioji (JP); Kazuaki Tamura, Hachioji (JP); Takeshi Ito, Hino (JP); Hiroyuki Kamee, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 130 days.

(21) Appl. No.: 14/812,084

(22) Filed: Jul. 29, 2015

(65) Prior Publication Data
US 2015/0327755 A1 Nov. 19, 2015

Related U.S. Application Data

(63) Continuation of application No. PCT/JP2014/051777, filed on Jan. 28, 2014.

(30) Foreign Application Priority Data

Jan. 29, 2013 (JP) ................................ 2013-014566

(51) Int. Cl.
*A61B 6/00* (2006.01)
*A61B 1/06* (2006.01)
(Continued)

(52) U.S. Cl.
CPC .......... *A61B 1/0638* (2013.01); *A61B 1/0653* (2013.01); *A61B 1/0661* (2013.01);
(Continued)

(58) Field of Classification Search
CPC ... A61B 1/0638; A61B 1/0653; A61B 1/0661; G01J 3/0218; G01J 3/10; G02B 23/2469
See application file for complete search history.

(56) References Cited

U.S. PATENT DOCUMENTS

| | | | | |
|---|---|---|---|---|
| 7,898,665 B2 * | 3/2011 | Brukilacchio | ....... | A61B 1/0653 356/417 |
| 2009/0167149 A1 | 7/2009 | Ito | | |
| 2012/0200687 A1 | 8/2012 | Kikuchi | | |

FOREIGN PATENT DOCUMENTS

| | | |
|---|---|---|
| CN | 102576795 A | 7/2012 |
| EP | 2 074 934 A2 | 7/2009 |

(Continued)

OTHER PUBLICATIONS

Japanese Office Action dated Oct. 25, 2016 in related Japanese Patent Application No. 2013-014566.
(Continued)

*Primary Examiner* — George Manuel
(74) *Attorney, Agent, or Firm* — Scully, Scott, Murphy & Presser, P.C.

(57) ABSTRACT

A light source device includes: excitation light sources configured to emit a plurality of excitation light including mutually different spectra; wavelength converting members configured to wavelength-convert the excitation light emitted from the excitation light sources into light having mutually different spectra and configured to be disposed in a common application region of the excitation light; and a light source control unit configured to switch a combination of the excitation light sources that are lighted among the excitation light sources based on the observation mode including a normal light observation mode and a special light observation mode to highlight a particular observation target input to an input unit, wherein light emitted from the wavelength converting members is used as illumination (Continued)

light, and the illumination light corresponding to the observation modes is emitted from a same emitting portion.

32 Claims, 9 Drawing Sheets

(51) Int. Cl.
  *G02B 23/24* (2006.01)
  *G01J 3/10* (2006.01)
  *G01J 3/02* (2006.01)

(52) U.S. Cl.
  CPC .............. *G01J 3/0218* (2013.01); *G01J 3/10* (2013.01); *G02B 23/2469* (2013.01)

(56) References Cited

FOREIGN PATENT DOCUMENTS

| | | |
|---|---|---|
| EP | 2 404 544 A1 | 1/2012 |
| EP | 2 482 349 A1 | 8/2012 |
| JP | 2005-205195 A | 8/2005 |
| JP | 2009-153712 A | 7/2009 |
| JP | 2009-297141 A | 12/2009 |
| JP | 2010-184047 A | 8/2010 |
| JP | 2010-213992 A | 9/2010 |
| JP | 2010-213993 A | 9/2010 |
| JP | 2012-105715 A | 6/2012 |
| JP | 2012-217484 A | 11/2012 |

OTHER PUBLICATIONS

English translation of International Preliminary Report on Patentability dated Aug. 13, 2015 together with the Written Opinion received in related International Application No. PCT/JP2014/051777.
Extended Supplementary European Search Report dated Sep. 6, 2016 received in PCT/JP2014/051777.
Chinese Office Action dated Jun. 20, 2016 in related Chinese Patent Application No. 201480006487.2.
Extended Supplementary European Search Report dated Sep. 6, 2016 received in Application No. 14 74 5448.2
Chinese Office Action dated Dec. 30, 2016 in related Chinese Patent Application No. 201480006487.2.
International Search Report dated Apr. 22, 2014 issued in PCT/JP2014/051777.

* cited by examiner

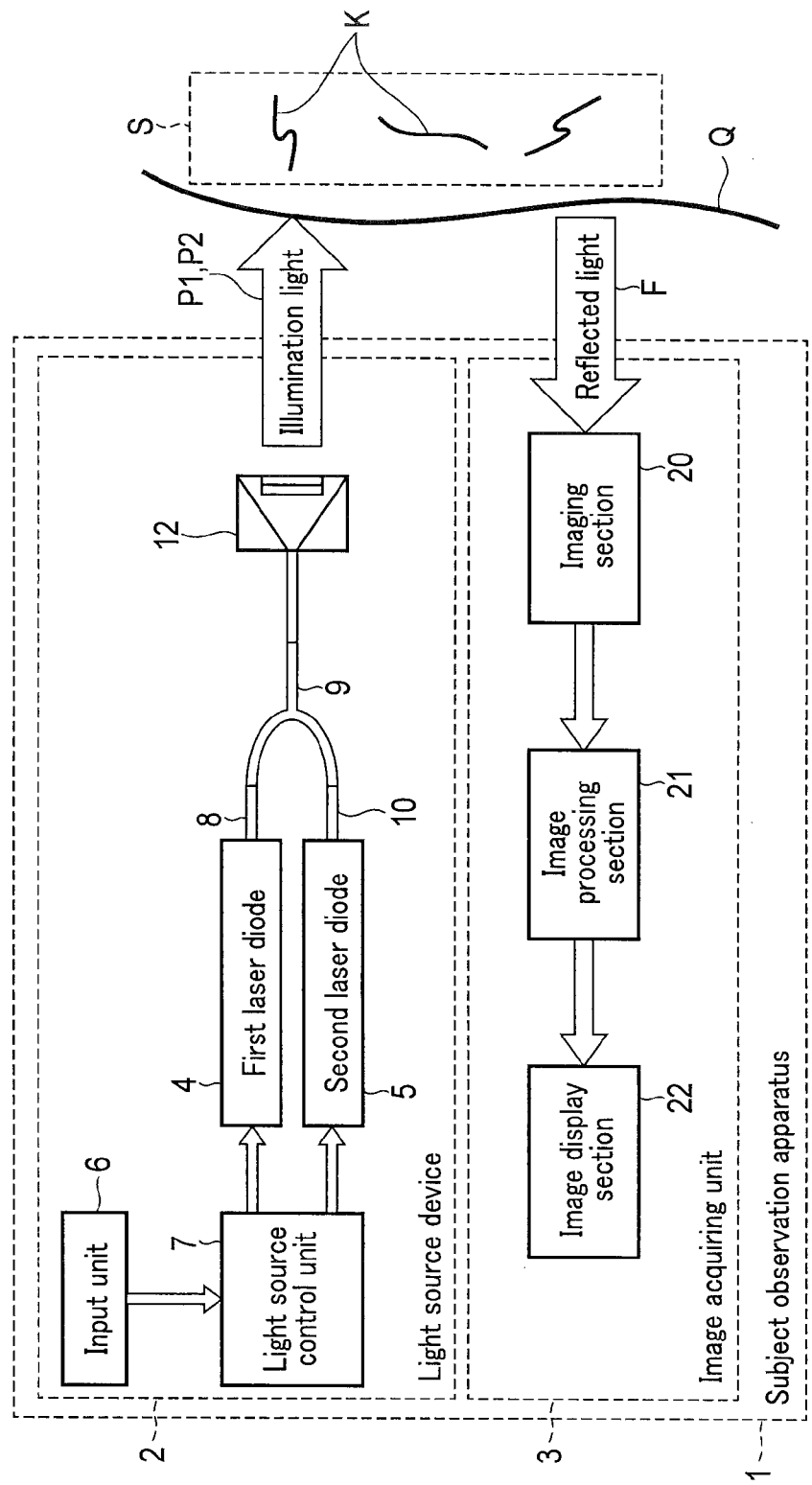
F I G. 1

Excitation and light emission spectra of first fluorescent material
(silicate-based (Eu-activated))

Excitation and light emission spectra of second fluorescent material (CaS (Eu-activated))

Light absorption coefficient of hemoglobin

Excitation and light emission spectra of YAG (Ce-activated)

Excitation and light emission spectra of third fluorescent material (SCA (Eu-activated))

LIGHT SOURCE DEVICE AND SUBJECT OBSERVATION APPARATUS AS WELL AS LIGHT SOURCE CONTROL METHOD

CROSS-REFERENCE TO RELATED APPLICATIONS

This application is a Continuation Application of PCT Application No. PCT/JP2014/051777, filed Jan. 28, 2014 and based upon and claiming the benefit of priority from the prior Japanese Patent Application No. 2013-14566, filed Jan. 29, 2013, the entire contents of which are incorporated herein by reference.

BACKGROUND OF THE INVENTION

1. Field of the Invention

The present invention relates to a light source device for performing observations such as a normal light observation in which white light is applied to a subject, and a special light observation by light having a particular wavelength (special light) to observe, for example, an observation target in a subject and relates to a subject observation apparatus including the light source device and a light source control method for controlling the light source device.

2. Description of the Related Art

There has been, for example, an endoscope as a subject observation apparatus including the light source device. The subject observation apparatus is provided with the light source device to apply, for example, the white light or special light to a subject. There has been a light source device wherein a small solid state light source is disposed at one end of an optical fiber and a wavelength converting member is disposed at the other end, output light of the solid state light source is guided to the wavelength converting member through the optical fiber, and this wavelength converting member converts the output light of the solid state light source into a desired irradiation pattern or wavelength (color). A technique of the light source device is shown in, for example, Jpn. Pat. Appln. KOKAI Publication No. 2005-205195 (Patent Literature 1). Patent Literature 1 relates to a light emitting apparatus and an endoscope including this light emitting apparatus, and discloses that excitation light generated from an excitation light source enters an optical fiber, this optical fiber guides the excitation light to an emitting portion disposed at a distal end of the optical fiber, a wavelength converting member provided in this emitting portion converts the wavelength, and the light having this converted wavelength is emitted as illumination light.

However, when the above light emitting apparatus emits a plurality of illumination light having different wavelengths, more than one emitting portion including wavelength converting members need to be prepared. Thus, in the endoscope including this light emitting apparatus, more than one emitting portion including wavelength converting members need to be prepared when, for example, more than one observation such as a normal light observation and a special light observation are performed. Therefore, the size reduction of the light emitting apparatus is difficult.

BRIEF SUMMARY OF THE INVENTION

An object of the present invention is to provide a light source device which does not need the preparation of more than one emitting portion and which enables the size reduction of the device and to provide a subject observation apparatus including the light source device and a light source control method for controlling the light source device.

According to a first aspect of the present invention, there is provided a light source device including excitation light sources configured to emit a plurality of excitation light including mutually different spectra, wavelength converting members configured to wavelength-convert the plurality of excitation light emitted from the excitation light sources into light having mutually different spectra and configured to be disposed in a common application region of the plurality of excitation light, an input unit configured to input observation modes including a normal light observation mode and a special light observation mode to highlight a particular observation target, and a light source control unit configured to switch a combination of the excitation light sources that are lighted among the excitation light sources based on the observation mode input to the input unit, wherein light emitted from the wavelength converting members is used as illumination light, and the illumination light corresponding to the observation modes is emitted from a same emitting portion.

According to a second aspect of the present invention, there is provided a subject observation apparatus including the light source device, the illumination light emitted from the light source device being applied to a subject, and an image acquiring unit configured to acquire image information regarding the subject.

According to a third aspect of the present invention, there is provided a light source control method including inputting one of observation modes including a normal light observation mode and a special light observation mode to highlight a particular observation target, switching a combination of excitation light sources that are lighted among excitation light sources based on the input observation mode information, emitting excitation light having mutually different spectra from the lighted excitation light sources and then applying the excitation light to wavelength converting members, and using light emitted from the wavelength converting members as illumination light, and emitting the illumination light corresponding to the observation modes from a same emitting portion.

According to the present invention, it is possible to provide a light source device which does not need the preparation of more than one emitting portion and which enables the size reduction of the device and to provide a subject observation apparatus including the light source device and a light source control method for controlling the light source device.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a configuration diagram showing a first embodiment of a subject observation apparatus including a light source device according to the present invention;

DETAILED DESCRIPTION OF THE INVENTION

[First Embodiment]

Figure 2:
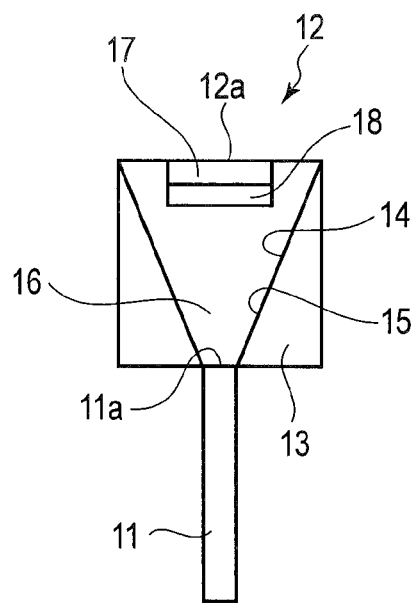
FIG. 2 is a schematic configuration diagram showing a wavelength converting unit in the same apparatus.

A first embodiment of the present invention is described below with reference to the drawings.

FIG. 1 shows a configuration diagram of a subject observation apparatus including a light source device. A subject observation apparatus 1 observes an observation target in a subject Q such as a living body, for example, hemoglobin flowing through a blood vessel K. The subject observation apparatus 1 includes more than one observation mode such as a normal light observation mode to apply white light to the subject Q, and a special light observation mode to highlight, for example, hemoglobin as an observation target.

The subject observation apparatus 1 includes a light source device 2 which applies illumination light P1 to the subject Q, and an image acquiring unit 3 which acquires image information regarding the subject Q. The subject Q is, for example, a human body, and is a living tissue including a blood vessel (including capillary vessels and thick blood vessels in deep parts) K.

The light source device 2 includes more than one excitation light source which emit more than one excitation light including mutually different spectra. The light source device 2 includes a first laser diode 4 as a first excitation light source, and a second laser diode 5 as a second excitation light source. The first laser diode 4 emits first excitation light having a central wavelength of 415 nm. The second laser diode 5 emits second excitation light having a central wavelength of 445 nm. The first and second laser diodes 4 and 5 are provided with an input unit 6 and a light source control unit 7 for driving and controlling these laser diodes 4 and 5.

The input unit 6 inputs observation mode information indicating more than one observation mode including the normal light observation mode, and the special light observation mode for highlighting a particular observation target. For example, the input unit 6 inputs the observation mode information in response to an operator's manual operations, or the observation mode information from an external computer.

The light source control unit 7 can switch when a combination of excitation light sources to be lighted among excitation light sources such as the first and second laser diodes 4 and 5 are input on the basis of the observation mode input to the input unit 6. For example, when one of the observation modes is input, the light source control unit 7 lights one of excitation light sources such as the first and second laser diodes 4 and 5 or simultaneously lights at least two excitation light sources in accordance with the observation mode.

Specifically, the light source control unit 7 switches between the lighting of the first laser diode 4 alone and the simultaneous lighting of the first and second laser diodes 4 and 5 on the basis of the observation mode information input to the input unit 6. The light source control unit 7 simultaneously lights the first and second laser diodes 4 and 5 if the normal light observation mode is input as the observation mode information. The light source control unit 7 lights the first laser diode 4 alone if the special light observation mode is input.

One entrance end of an optical coupler 9 is optically connected to the first laser diode 4 via a first optical fiber 8. The first optical fiber 8 guides the first excitation light emitted from the first laser diode 4 to the optical coupler 9.

The other entrance end of an optical coupler 9 is optically connected to the second laser diode 5 via a second optical fiber 10. The second optical fiber 10 guides the second excitation light emitted from the second laser diode 5 to the optical coupler 9.

A wavelength converting unit 12 is optically connected to the emission end of the optical coupler 9 via a third optical fiber 11. The optical coupler 9 multiplexes the first excitation light guided by the first optical fiber 8 and the second excitation light guided by the second optical fiber 10.

The third optical fiber 11 guides the excitation light (multiplexed excitation light) multiplexed by the optical coupler 9 to the wavelength converting unit 12.

FIG. 2 shows a schematic configuration diagram of the wavelength converting unit 12. The wavelength converting unit 12 converts the wavelengths of the excitation light emitted from excitation light sources such as the first and second laser diodes 4 and 5 into light having different spectra, respectively. Specifically, the wavelength converting unit 12 is provided at the distal end of the light source device 2, and converts the wavelength of the multiplexed excitation light guided by the third optical fiber 11 and emits the light as the illumination light P1. The wavelength converting unit 12 includes a holder 13, and an emission end 11a of the third optical fiber 11 is connected to the holder 13. A slanted concave surface portion 14 in which the inner circumferential surface is tapered is provided in the holder 13. The slanted concave surface portion 14 is formed so that the opening degree of the tapered shape increases toward an emission hole 12a for the illumination light P1, and a reflective member 15 is formed on the surface of the tapered shape.

The reflective member 15 reflects, toward the emission hole 12a, the multiplexed excitation light emitted from the emission end 11a of the third optical fiber 11, and a fluorescence generated by a first fluorescent material 17 and a second fluorescent material 18. A light transmitting member 16 is provided in the space of the tapered shape of the slanted concave surface portion 14.

The first fluorescent material 17 and the second fluorescent material 18 are provided in a stacked state on the side of the emission hole 12a of the light transmitting member 16. The light transmitting member 16 transmits the multiplexed excitation light emitted from the third optical fiber 11, and also transmits first and second fluorescences generated from the first and second fluorescent materials 17 and 18.

The first fluorescent material 17 is disposed on the side of the emission end 11a of the third optical fiber 11. The second fluorescent material 18 is disposed on the side of the emission hole 12a of the light transmitting member 16. The first fluorescent material 17 and the second fluorescent material 18 are provided in a stacked state on the optical axis of the multiplexed excitation light emitted from the emission end 11a of the third optical fiber 11 in a region where the application region of the first excitation light and the application region of the second excitation light overlap, that is, in a common application region of the first and second excitation light.

The first fluorescent material 17 emits light having a third spectrum that is longer in wavelength than the first spectrum and that is different from the second spectrum when the first excitation light is applied.

The second fluorescent material 18 emits light having a fourth spectrum that is longer in wavelength than the second spectrum and that is different from the first and third spectra when the second excitation light is applied.

Specifically, the first fluorescent material 17 generates the first fluorescence having a spectrum different from those of the first excitation light and the second excitation light.

The second fluorescent material 18 generates the second fluorescence including a spectrum different from those of the first excitation light, the second excitation light, and the first fluorescence.

The second fluorescent material 18 includes properties of absorbing and emitting the first fluorescence generated by the first fluorescent material 17. Thus, the first and second fluorescent materials 17 and 18 are preferably stacked so that the second fluorescent material 18 and the first fluorescent material 17 are arranged in this order toward the emission hole 12a to prevent the first fluorescence generated from the first fluorescent material 17 toward the emission hole 12a from being absorbed by the second fluorescent material. The second fluorescence generated from the second fluorescent material 18 is not absorbed by the first fluorescent material 17.

Figure 3:
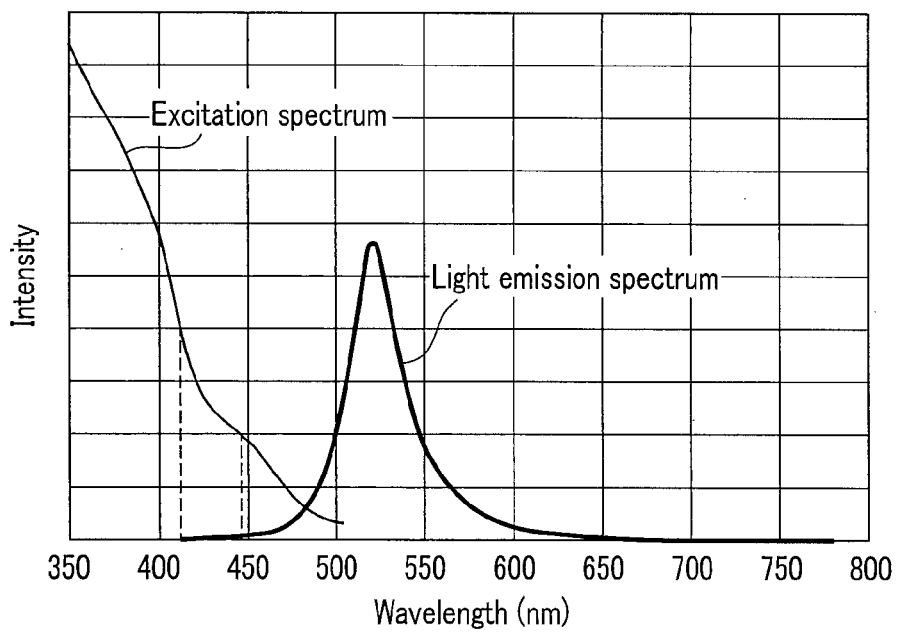
FIG. 3 is a graph showing excitation and light emission spectra of a first fluorescent material (silicate-based (Eu-activated)) in the same apparatus.

FIG. 3 shows an excitation spectrum and a light emission spectrum of the first fluorescent material 17 (silicate-based (Eu-activated)). The excitation spectrum is the wavelength dependence of the excitation light on light emission intensity. The light emission spectrum is a wavelength distribution of the light emission intensity when the first fluorescent material 17 is excited and generates light, and the peak wavelength is 517 nm.

As obvious from the excitation spectrum, the first fluorescent material 17 is excited and generates light in response to both the first excitation light having the central wavelength of 415 nm emitted from the first laser diode 4 and the second excitation light having the central wavelength of 445 nm emitted from the second laser diode 5. The rate of excitation and light generation attributed to the second excitation light is lower than the rate of excitation and light generation attributed to the first excitation light, and is about 40%.

Figure 4:
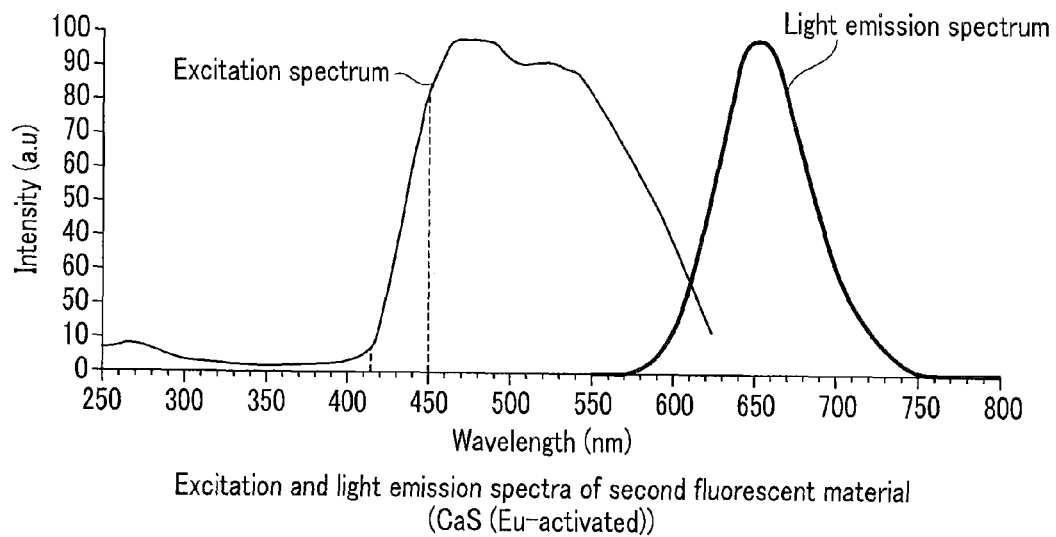
FIG. 4 is a graph showing excitation and light emission spectra of a second fluorescent material (CaS (Eu-activated)) in the same apparatus.

FIG. 4 shows an excitation spectrum and a light emission spectrum of the second fluorescent material 18 (silicate-based (Eu-activated CaS)). The peak wavelength of the light emission spectrum is 650 nm. As obvious from the excitation spectrum shown in FIG. 4, the second fluorescent material 18 hardly generates light in response to the first excitation light having the central wavelength of 415 nm generated from the first laser diode 4, whereas the second fluorescent material 18 is excited and generates light in response to the second excitation light having the central wavelength of 445 nm generated from the second laser diode 5.

The first and second fluorescent materials 17 and 18 are formed respectively by solidifying in a condition in which powder of a fluorescent material is dispersed in a sealing material such as a transparent resin or glass. The thickness of the first and second fluorescent materials 17 and 18 and the concentration conditions of the powdered fluorescent material dispersed in the sealing material are set so that the first and second excitation light may be converted into first and second fluorescences having desired wavelengths when the first and second excitation light is applied, respectively.

The first and second fluorescent materials 17 and 18 absorb some of the first and second excitation light and generate light and transmit some of the first and second excitation light. Meanwhile, the amounts of the excitation light transmitted in the first and second fluorescent materials 17 and 18 are also adjusted by the thickness and concentrations of the first and second fluorescent materials 17 and 18.

The image acquiring unit 3 acquires the image information regarding the subject Q, and includes an imaging section 20, an image processing section 21, and an image display section 22.

The imaging section 20 images reflected light F when the illumination light P1 is applied to the subject Q by the light source device 2, and the imaging section 20 sends an image signal acquired by the imaging to the image processing section 21. The imaging section 20 includes an image sensor in which red pixels (R), green pixels (G), and blue pixels (B) are arrayed. The red pixel, the green pixel, and the blue pixel output light receiving signals corresponding to light receiving amounts, respectively. The imaging section 20 generates an image signal from the light receiving signals respectively output from the red pixels, the green pixels, and the blue pixels, and outputs the image signal.

The image signal output from the imaging section 20 is input to the image processing section 21, and the image processing section 21 subjects this image signal to image processing adapted to either the normal light observation mode or the special light observation mode.

In the special light observation mode, the image signal output from the imaging section 20 is input to the image processing section 21, and the image processing section 21 subjects this image signal to image processing to generate a special light observation image. That is, the image processing section 21 performs signal processing to allocate the light receiving signal of the blue pixel to the light receiving signals of the blue and green pixels from the image signal output from the imaging section 20 and allocate the light receiving signal of the green pixel to the light receiving signal of the red pixel, and subjects the processed signal to preset image processing to generate special light observation image.

In the special light observation image, a capillary vessel K in the surface layer of a mucous membrane has an approximately brown color in which bright red, dark green, and dark blue are mixed. A thick blood vessel K in a deep part has an approximately blue-green color in which dark red, bright green, and bright blue are mixed. As a result, the contrast between the capillary vessel K in the surface layer of the mucous membrane and the thick blood vessel K in the deep part is enhanced in the special light observation image.

Figure 5:
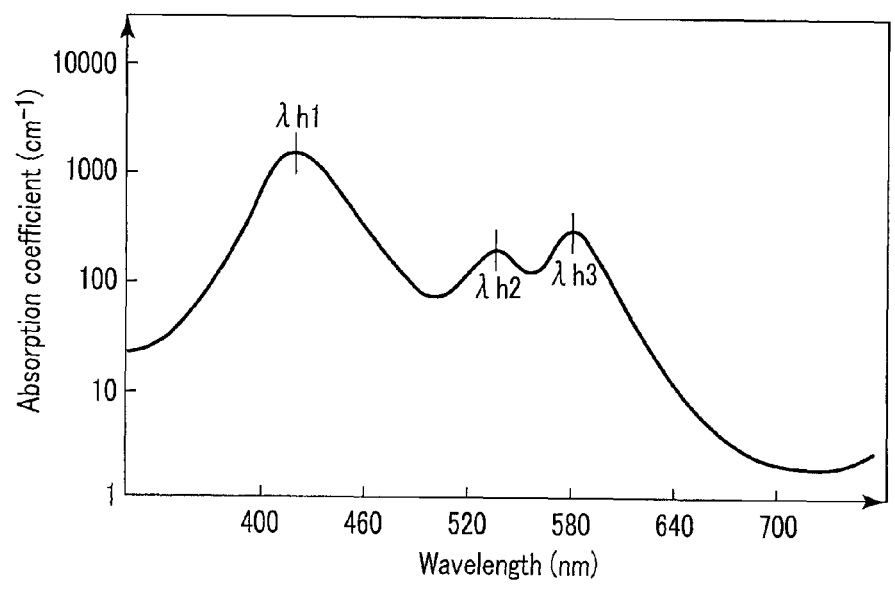
FIG. 5 is a graph showing a light absorption coefficient of hemoglobin in a blood vessel in a living tissue which is an observation target in the same apparatus.

The generation of the special light observation image is specifically described. In the illumination light P1 in the special light observation mode, the spectrum of the first excitation light emitted from the first laser diode 4 exists in the vicinity of a maximum observation peak ($\lambda$h1) of a light absorption spectrum of hemoglobin as shown in FIG. 5. The spectrum of the first fluorescence exists in the vicinity of an intensity peak ($\lambda$h2) of the light absorption spectrum of hemoglobin.

The first excitation light having the wavelength of about 415 nm is strongly absorbed by the hemoglobin in the capillary vessel K in the surface layer of the mucous membrane. The first excitation light having the wavelength of about 415 nm has the properties of being easily scattered in the part of the surface layer of the mucous membrane where the blood vessel K is not present, and therefore does not reach deep parts.

In contrast, the first fluorescence having a wavelength of about 520 nm is not easily scattered compared to the first excitation light having the wavelength of about 415 nm, reaches deep parts in the mucous membrane, and is much absorbed in the hemoglobin in the blood vessel K in the deep parts.

The reflected light F reflected when the illumination light 21 is applied to the subject is received by the red pixels, the green pixels, and the blue pixels of the image sensor in the imaging section 20.

A light component mainly received by the blue pixel is the reflected light F of the first excitation light having the wavelength of about 415 nm. The amount of the reflected light F of the first excitation light is small in the capillary vessel part in the surface layer of the mucous membrane.

A light component mainly received by the green pixel is the reflected light F of the first excitation light having the wavelength of about 415 nm. The amount of the reflected light F of the first excitation light is small in the thick blood vessel part in the deep part.

A red region in the illumination light P1 is a wavelength lacking region, and does not include light in the red region, so that the red pixel hardly receives the reflected light F.

Thus, the light receiving signals of the blue, green, and red pixels output from the image sensor of the imaging section 20 are transmitted to the image processing section 21.

As described above, the image processing section 21 performs signal processing to allocate the light receiving signal of the blue pixel as the light receiving signals of the blue and green pixels and allocate the light receiving signal of the green pixel as the light receiving signal of the red pixel, and subjects the processed signal to preset image processing to generate the special light observation image.

In the normal light observation mode, the image signal output from the imaging section 20 is input to the image processing section 21, and the image processing section 21 performs image processing in such a manner that the light receiving signals of blue, green, and red of this image signal are pixel signals of the same color to generate a normal light observation image. That is, the image processing section 21 performs signal processing in such a manner that the light receiving signal of the blue pixel is the light receiving signal of each pixel of blue, the light receiving signal of the green pixel is the light receiving signal of the green pixel, and the light receiving signal of the red pixel is the light receiving signal of the red pixel from the pixel signals output from the imaging section 20, and the image processing section 21 subjects the processed signal to preset image processing to generate the normal light observation image. The normal light observation image becomes an image including, for example, the capillary vessel K in the surface layer of the mucous membrane resulting from the application of the white light.

The normal light observation mode is suited to a normal observation. There are light having various wavelengths due to the application of the white light to the subject, and there are various absorption and scattering characteristics regarding the subject. In the normal light observation mode, pixels can not be allocated in contrast with the special light observation mode, so that the contrast between the capillary vessel K in the surface layer of the mucous membrane and the thick blood vessel K in the deep part can not be highlighted.

The image display section 22 performs processing to display the special light observation image or the normal light observation image generated by the image processing section 21 on a monitor in accordance with either the special light observation mode or the normal light observation mode, and displays the processed special light observation image or normal light observation image on the monitor. In the special light observation mode, as described above, a special light observation image of the subject Q in which, for example, the capillary vessel K in the surface layer of the mucous membrane is brown and the thick blood vessel K in the deep part is blue-green is generated. Consequently, the image display section 22 displays, on the monitor, the special light observation image with enhanced contrast in which the capillary vessel K in the surface layer of the mucous membrane is brown and the thick blood vessel K in the deep part is blue-green.

Next, the operation of the apparatus having the above configuration is described.

[When the Subject Q is Observed in the Special Light Observation Mode]

If the special light observation mode is input to the input unit 6 as the observation mode information, the input unit 6 sends information regarding the special light observation mode to the light source control unit 7. If the special light observation mode is input, the light source control unit 7 lights the first laser diode 4 alone.

The first laser diode 4 emits the first excitation light having the central wavelength of 415 nm by lighting. The first excitation light is guided to the wavelength converting unit 12 provided at the distal end of the light source device 2 through the first optical fiber 8, the optical coupler 9, and the third optical fiber 11, and enters the wavelength converting unit 12.

The wavelength converting unit 12 converts the wavelength of the first excitation light that has entered, and emits the light as the illumination light P1 for special light. This illumination light P1 for special light is applied to the subject Q.

To observe the subject Q, a reflected light FF from the subject Q when the illumination light P1 is applied to the subject Q is imaged, and an image obtained by the imaging is observed. Therefore, how the illumination light P1 is scattered and absorbed in the living tissue or the blood vessel of the subject Q greatly affects how the subject Q appears.

In the present embodiment, the blood vessel K of the subject Q is highlighted and observed in the special light observation mode. FIG. 5 shows a light absorption coefficient of hemoglobin flowing through the blood vessel K. The absorption coefficient of hemoglobin has absorption intensity peaks at three different wavelengths in a visible light region of a wavelength region of 380 nm to 780 nm: around a wavelength of 415 nm ($\lambda h1$), around a wavelength of 540 nm ($\lambda h2$), and around a wavelength of 580 nm ($\lambda h3$). Among the above, the absorption intensity around the wavelength of 415 nm is the highest.

In the special light observation mode, the blood vessel K of the subject Q is highlighted and observed by the use of the difference of the light absorption coefficient attributed to the wavelengths.

The spectrum of the illumination light P1 in the special light observation mode is described. Here, a wavelength region in which spectral intensity is less than or equal to a predetermined value, for example, less than or equal to one twentieth of the maximum intensity of the light emission spectrum in the visible light region (having a wavelength of 400 nm to 780 nm) is defined as a wavelength lacking region.

Figure 6:
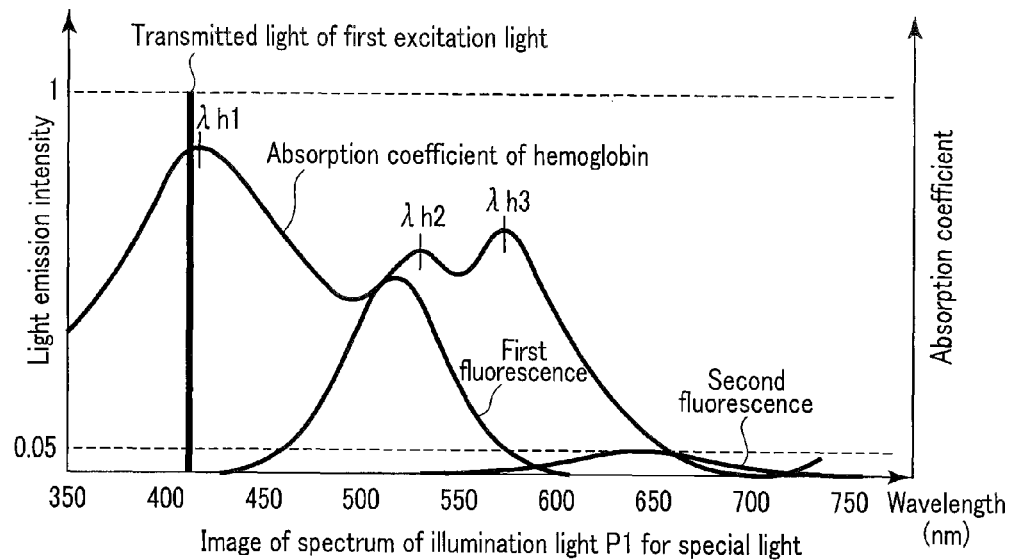
FIG. 6 is a graph showing a spectrum of first illumination light P1 emitted from the same apparatus.

FIG. 6 shows a spectrum of the illumination light P1 for special light. The first excitation light having the central wavelength of 415 nm excites the first fluorescent material 17. As a result of this excitation, the first fluorescent material 17 generates the first fluorescence having a peak wavelength of about 517 nm and a light emission wavelength region of about 500 nm to 550 nm.

The illumination light P1 for special light emitted from the light source device 2 is light which is the mixture of the first fluorescence generated from the first fluorescent material 17, the second fluorescence generated from the second fluorescent material 18, and the first excitation light which has not been absorbed by and has passed through the first fluorescent material 17. The spectrum of the illumination light P1 is a spectrum which is the mixture of the spectrum of the first fluorescence, the spectrum of the second fluorescence, and the spectrum of the first excitation light.

The first excitation light hardly excites the second fluorescent material 18 as shown in FIG. 4. Thus, the spectral intensity of the second fluorescence is less than or equal to one twentieth of the intensity of the transmitted light of the first excitation light which is the maximum intensity of the illumination light P1.

Therefore, the region (region having a wavelength longer than about 580 nm) of the illumination light P1 for special light having a wavelength longer than that of the spectrum of the first fluorescence is a second wavelength lacking region. There is also a first wavelength lacking region between the spectrum of the transmitted light of the first excitation light and the spectrum of the first fluorescence (around 420 nm to around 480 nm).

The spectrum of the first excitation light included in the illumination light P1 for special light exists in the vicinity of the maximum intensity peak ($\lambda h1$) of the light absorption spectrum of hemoglobin as shown in FIG. 5. The spectrum of the first fluorescence exists in the vicinity of the intensity peak ($\lambda h2$) of the light absorption spectrum of hemoglobin.

Between the first excitation light having the wavelength of about 415 nm which has not been absorbed by and has passed through the first fluorescent material 17 (hereinafter referred to as the transmitted light of the first excitation light) and the first fluorescence having the wavelength of about 520 nm, there are differences of reflection and scattering characteristics regarding the living tissue of the subject Q and the depth of penetration into the living tissue, and there is also difference of absorption parts in the living tissue of the subject Q. Thus, the reflected light F when the transmitted light of the first excitation light is applied to the subject Q and the reflected light F when the first fluorescence is applied to the subject Q include contrast.

Specifically, when the surface layer of the mucous membrane of the subject Q is observed in the special light observation mode, the transmitted light of the first excitation light having the wavelength of about 415 nm has the properties of being strongly absorbed by the hemoglobin in the capillary vessel K in the surface layer of the mucous membrane and being strongly reflected and scattered in the part of the surface layer of the mucous membrane where the blood vessel K is not present.

In contrast, if applied to the part of the surface layer of the mucous membrane where the blood vessel K is not present, the first fluorescence having the wavelength of about 520 nm penetrates the mucous membrane deeper than the transmitted light of the first excitation light. The first fluorescence is then scattered and reflected, and absorbed by the hemoglobin in the thick blood vessel K in the deep part.

In such a condition, the imaging section 20 images the reflected light F when the illumination light P1 for special light is applied to the subject Q, and the imaging section 20 outputs an image signal acquired by this imaging.

The image signal output from the imaging section 20 is input to the image processing section 21, and the image processing section 21 performs signal processing to allocate the light receiving signal of the blue pixel to the light receiving signals of the blue and green pixels from the image signal and allocate the light receiving signal of the green pixel to the light receiving signal of the red pixel. The image processing section 21 subjects the processed signal to preset image processing, and generates a special light observation image such that the capillary vessel K in the surface layer of the mucous membrane has an approximately brown color in which bright red, dark green, and dark blue are mixed and such that a thick blood vessel K in a deep part has an approximately blue-green color in which dark red, bright green, and bright blue are mixed.

The image display section 22 performs processing to display the special light observation image generated by the image processing section 21 on the monitor in accordance with the special light observation mode, and displays the processed special light observation image on the monitor. As described above, the special light observation image is displayed as an image in which, for example, the capillary vessel K in the surface layer of the mucous membrane is brown, the thick blood vessel K in the deep part is blue-green, and the contrast between the capillary vessel K in the surface layer of the mucous membrane and the thick blood vessel K in the deep part is enhanced.

The lights in the wavelength region between the spectrum of the transmitted light of the first excitation light and the spectrum of the first fluorescence (around 420 nm to around 480 nm) and in the wavelength region having a wavelength longer than that of the spectrum of the first fluorescence affect as image noise when the contrast is enhanced.

Therefore, to obtain an image having slight image noise and having high contrast, the spectral intensity is preferably less than or equal to one twentieth of the maximum intensity of the light emission spectrum in the visible light region (having a wavelength of 400 nm to 780 nm) in the wavelength region between the spectrum of the transmitted light of the first excitation light and the spectrum of the first fluorescence and in the wavelength region having a wavelength longer than that of the spectrum of the first fluorescence.

The first excitation light emitted from the first laser diode 4 is not limited to the central wavelength of 415 nm, and has only to be a light which includes a spectrum in the vicinity of the wavelength $\lambda h1$ where the absorption coefficient of hemoglobin is high and which can excite the first fluorescent material 17 and which has a wavelength lacking region between the spectrum of the first excitation light and the spectrum of the first fluorescence.

The first fluorescent material 17 is not limited to the Eu-activated silicate-based fluorescent material, and has only to be a material which includes a spectrum in the vicinity of the wavelength $\lambda h2$ where the absorption coefficient of hemoglobin is high and which has a wavelength lacking region between the spectrum of the transmitted light of the first excitation light and the spectrum of the first fluorescence.

[When the Mode is Switched from the Special Light Observation Mode to the Normal Light Observation Mode to Observe the Subject Q]

If the observation mode information to switch from the special light observation mode to the normal light observation mode is input to the input unit 6, information regarding the normal light observation mode is sent to the light source control unit 7 from the input unit 6. If the normal light observation mode is input, the light source control unit 7 lights the second laser diode 5 in addition to the first laser diode 4 which is being lighted, leading to the two-light simultaneous lighting state.

The first excitation light having the central wavelength of 415 nm emitted from the first laser diode 4 enters the first optical fiber 8, and is guided to the optical coupler 9 by the first optical fiber 8. In addition, the second excitation light having a central wavelength of 445 nm emitted from the second laser diode 5 enters the second optical fiber 10, and is guided to the optical coupler 9 by the second optical fiber 10.

The optical coupler 9 multiplexes the first excitation light guided by the first optical fiber 8 and the second excitation light guided by the second optical fiber 10, and sends the multiplexed excitation light to the third optical fiber 11. The third optical fiber 11 guides the multiplexed excitation light to the wavelength converting unit 12 by the optical coupler 9.

The wavelength converting unit 12 converts the wavelength of the multiplexed excitation light guided by the third optical fiber 11, and emits the light as an illumination light (white light) P2 for normal light. The illumination light P2 is applied to the subject Q.

Figure 7:
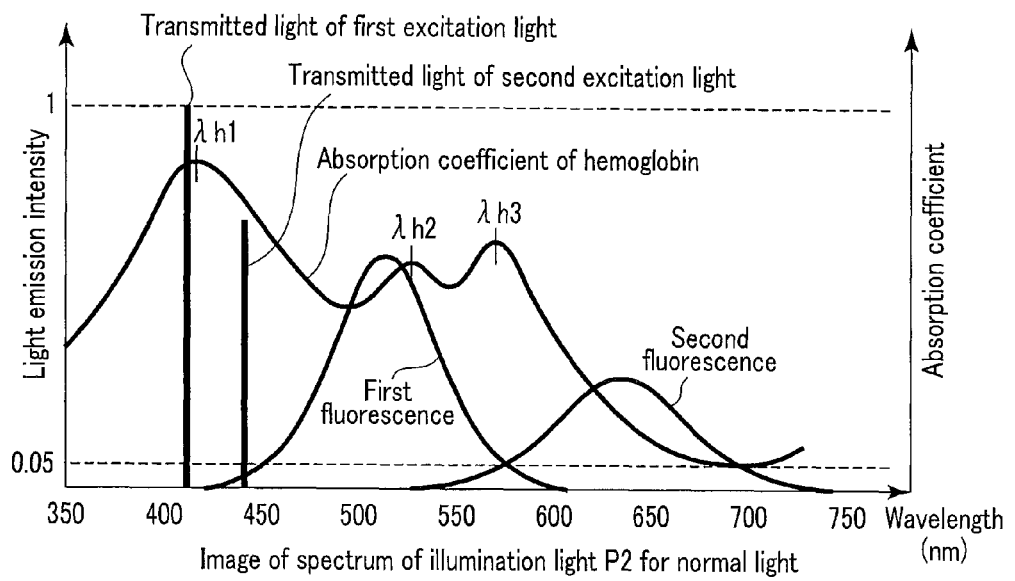
FIG. 7 is a graph showing a spectrum of first illumination light P2 emitted from the same apparatus.

The spectrum of the illumination light P2 in the normal light observation mode is described. FIG. 7 shows a spectrum of the illumination light P2 for normal light. The second excitation light having a central wavelength of 445 nm excites the second fluorescent material 18. The second fluorescent material 18 generates the second fluorescence having a peak wavelength of about 650 nm and a light emission wavelength region of about 630 nm to 690 nm.

In contrast with the illumination light P1 in the special light observation mode, the illumination light P2 for normal light emitted from the light source device 2 is the addition of the second fluorescence and the second excitation light which has not been absorbed by and has passed through the second fluorescent material 18. The spectrum of the illumination light P2 is a spectrum in which the spectrum of the second fluorescence and the spectrum of the second excitation light are added to the spectrum of the illumination light P1.

That is, in the spectrum of the illumination light P2 for normal light, the spectrum of the second excitation light having the central wavelength of 445 nm is added to the wavelength region (around 420 nm to around 480 nm) which is the wavelength lacking region between the spectrum of the first excitation light and the spectrum of the first fluorescence in the illumination light P1 in the special light observation mode. Moreover, in the spectrum of the illumination light P2 for normal light, the spectrum of the second fluorescence (having a peak wavelength of 650 nm) is added to the wavelength region (around 580 nm and over) on the longer wavelength side than the spectrum of the first fluorescence.

The illumination light P2 in the normal light observation mode obtains the white light by adding a spectrum to the wavelength lacking region of the illumination light P1 for special light. The second excitation light also excites the first fluorescent material 17. The light emission intensity of the first fluorescence attributed to the second excitation light is lower than the light emission intensity of the first fluorescence attributed to the first excitation light. Thus, the second excitation light is added, and the first and second laser diodes 4 and 5 are simultaneously lighted, whereby the light emission intensity of the first fluorescence does not become excessively high, and the light amounts of the first and second excitation light can be adjusted respectively by the light source control unit 7 so that the illumination light P2 for normal light will be the white light.

The second excitation light emitted from the second laser diode 5 is not limited to the central wavelength of 445 nm, and has only to be light which can excite the second fluorescent material 18 and which has a spectrum in the wavelength lacking region between the spectrum of the first fluorescence and the spectrum of the first excitation light.

Figure 8:
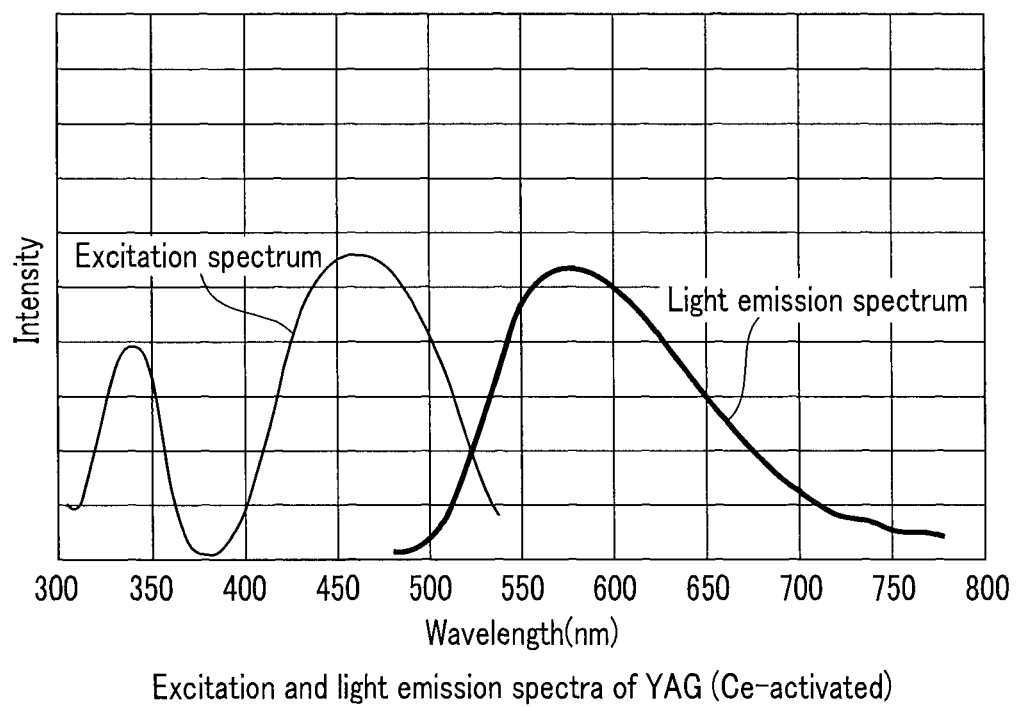
FIG. 8 is a graph showing an excitation spectrum and a light emission spectrum of YAG (Ce-activated) applicable to the same apparatus.

The second fluorescent material 18 is not limited to Eu-activated CaS, and has only to be a fluorescent material which generates light by the second excitation light and which includes a light emission spectrum on the longer wavelength side than the first fluorescence as in Ce-activated YAG (yellow) and which hardly generates light in response to the first excitation light. FIG. 8 shows an excitation spectrum and a light emission spectrum of YAG (Ce-activated).

The imaging section 20 images the reflected light F when the illumination light P2 is applied to the subject Q, and the imaging section 20 outputs an image signal acquired by this imaging.

The image signal output from the imaging section 20 is input to the image processing section 21, and the image processing section 21 performs image processing in such a manner that the light receiving signals of blue, green, and red of this image signal are pixel signals of the same color to generate a normal light observation image. That is, the image processing section 21 performs signal processing in such a manner that the light receiving signal of the blue pixel is the light receiving signal of each pixel of blue, the light receiving signal of the green pixel is the light receiving signal of the green pixel, and the light receiving signal of the red pixel is the light receiving signal of the red pixel from the pixel signals output from the imaging section 20, and the image processing section 21 subjects the processed signal to preset image processing to generate the normal light observation image.

The image display section 22 performs processing to display the normal light observation image generated by the image processing section 21 on the monitor in accordance with the normal light observation mode, and displays the processed normal light observation image on the monitor.

Thus, according to the first embodiment described above, the emission end of the first laser diode 4 and the emission end of the second laser diode 5 are connected to the optical coupler 9, respectively, and the emission end of the optical coupler 9 is connected to the wavelength converting unit 12. In the special light observation mode, the first laser diode 4 alone is lighted. In the normal light observation mode, the first and second laser diodes 4 and 5 are simultaneously lighted. Consequently, it is possible to perform, in the single wavelength converting unit 12, the special light observation for generating the special light observation image with enhanced contrast in which the capillary vessel K in the surface layer of the mucous membrane is approximately brown and the thick blood vessel K in the deep part is approximately blue-green in the special light observation mode, and the normal light observation by white light application for displaying the capillary vessel K in the surface layer of the mucous membrane in the normal light observation mode, and the size reduction is possible.

In the special light observation mode, the transmitted light of the first excitation light having the wavelength of about 415 nm which has passed through the first and second fluorescent materials 17 and 18 is strongly absorbed by the hemoglobin in the capillary vessel K in the surface layer of the mucous membrane and, and strongly reflected and scattered in the part of the surface layer of the mucous membrane where the blood vessel K is not present. The first fluorescence having the wavelength of about 520 nm penetrates the mucous membrane deeper than the transmitted light of the first excitation light and then scattered and reflected, and absorbed by the hemoglobin in the thick blood vessel K in the deep part. As a result, it is possible to observe the capillary vessel K in the surface layer of the mucous membrane and the thick blood vessel K in the deep part in the subject Q in a high-contrast image, and easily discover, for example, a cancer that changes the capillary vessel in the surface layer of the mucous membrane.

The first excitation light having the wavelength of about 415 nm is a narrow-band laser light emitted by the first laser diode 4, so that a microstructure such as the capillary vessel K is easily observed.

In the normal light observation mode, the first and second laser diodes 4 and 5 are simultaneously lighted, or the second laser diode 5 is lighted in addition to the first laser diode 4 which is being limited, so that two light is simultaneously lighted. Thus, it is possible to obtain the white light by adding the spectrum of the second fluorescence to the wavelength region which is the wavelength lacking region in the illumination light P1 in the special light observation mode.

The first and second laser diodes 4 and 5 may be replaced by LEDs which emit excitation light having similar wavelength bands.

[Second Embodiment]

Next, a second embodiment of the present invention is described with reference to the drawings. The same parts as those in FIG. 1 are provided with the same signs, detailed descriptions thereof are omitted.

Figure 9:
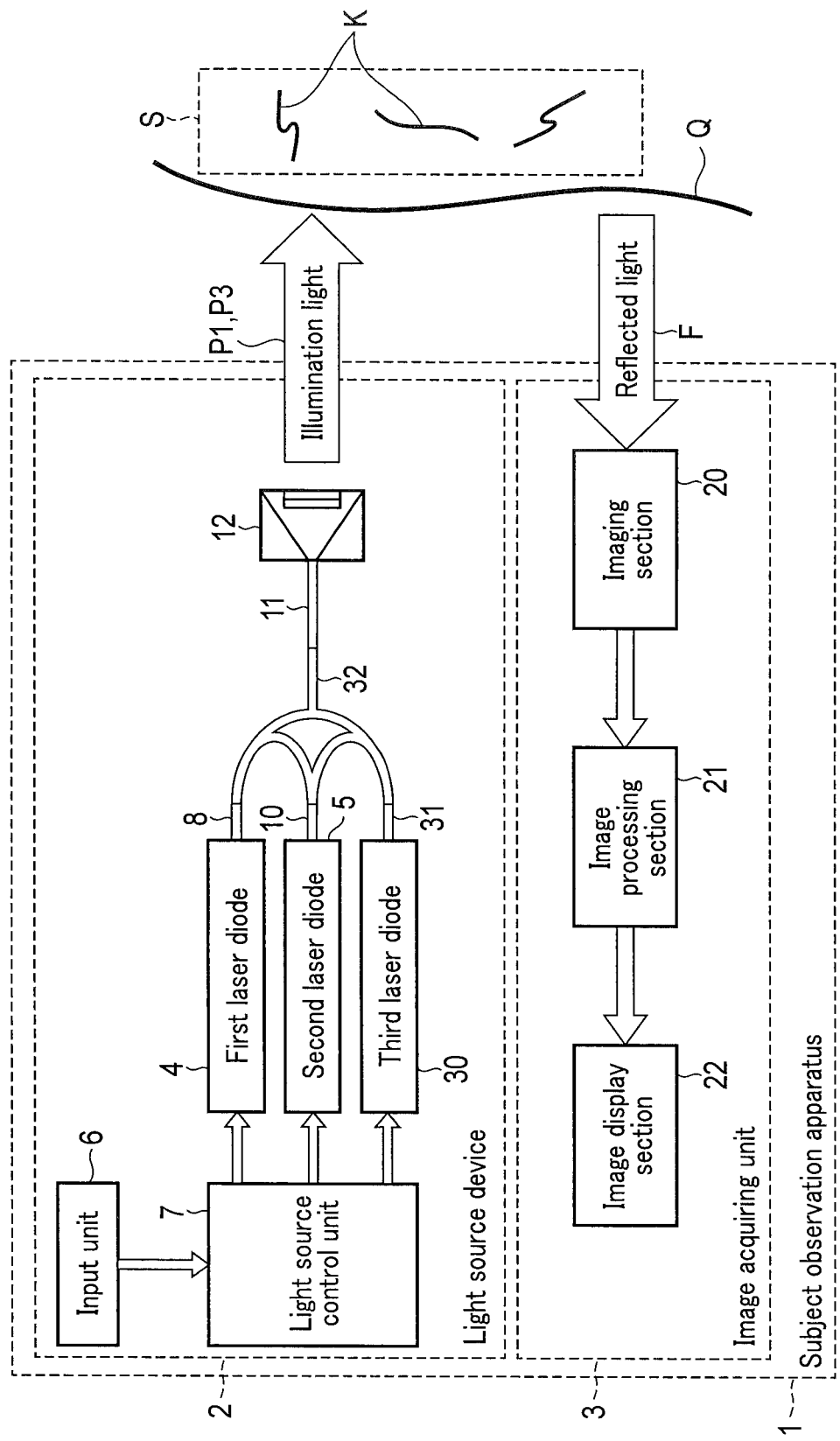
FIG. 9 is a configuration diagram showing a second embodiment of a subject observation apparatus including a light source device according to the present invention.

FIG. 9 shows a configuration diagram of a subject observation apparatus including a light source device. The subject observation apparatus 1 is provided with a third laser diode 30 in addition to the first and second laser diodes 4 and 5. The third laser diode 30 emits third excitation light having a central wavelength of 375 nm. The third laser diode 30 is optically connected to one entrance end of an optical coupler 32 via a fourth optical fiber 31. The fourth optical fiber 31 guides the third excitation light emitted from the third laser diode 30 to the optical coupler 32.

If the special light observation mode is input from the input unit 6, the light source control unit 7 lights the first laser diode 4 alone to emit the illumination light P1 for special light. If the normal light observation mode is input, the light source control unit 7 simultaneously lights the first, second, and third laser diodes 4, 5, and 30 to emit an illumination light P3 for normal light.

The optical coupler 32 is optically connected to the respective entrance ends of the first optical fiber 8, the second optical fiber 10, and the fourth optical fiber 31. The optical coupler 32 multiplexes the first excitation light guided by the first optical fiber 8, the second excitation light guided by the second optical fiber 10, and the third excitation light guided by the fourth optical fiber 31, and guides the multiplexed excitation light to the third optical fiber 11.

Figure 10:
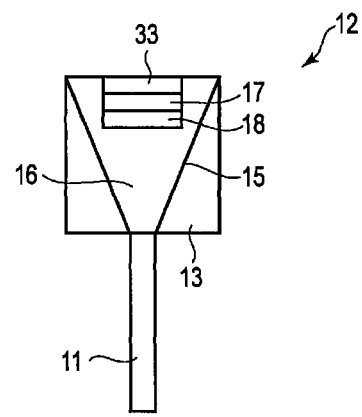
FIG. 10 is a schematic configuration diagram showing a wavelength converting unit in the same apparatus.

FIG. 10 shows a configuration diagram of the wavelength converting unit 12. The single wavelength converting unit 12 includes a third fluorescent material 33 in addition to the first and second fluorescent materials 17 and 18. The second fluorescent material 18 is disposed on the side of the emission end 11a of the third optical fiber 11. The third fluorescent material 33 is disposed on the side of the emission hole 12a in the light transmitting member 16. The first fluorescent material 17 is disposed between the second and third fluorescent materials 18 and 33. The first, second, and third fluorescent materials 17, 18, and 33 are provided in a stacked state on the optical axis of the multiplexed excitation light emitted from the emission end 11a of the third optical fiber 11 in a region where the application regions of the first, second, and third excitation light overlap.

Figure 11:
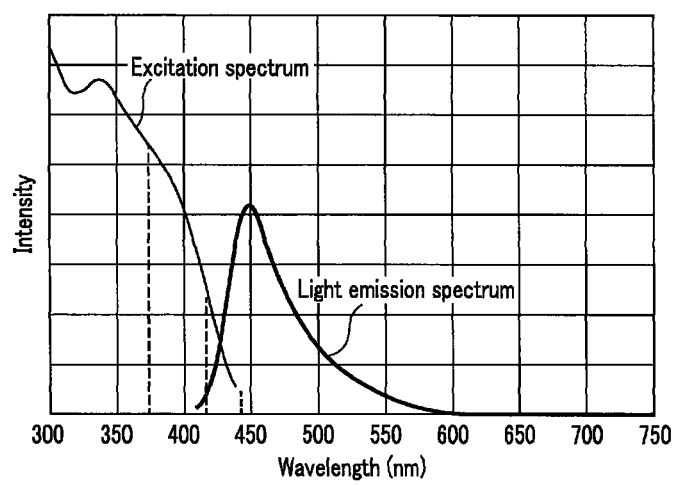
FIG. 11 is a graph showing excitation and light emission spectra of a third fluorescent material in the same apparatus.

FIG. 11 shows excitation and light emission spectra of the third fluorescent material 33. The third fluorescent material 33 generates a third fluorescence having a spectrum different from those of the first, second, and third excitation light and the first and second fluorescences.

The third fluorescent material 33 is Eu-activated (Sr, Ca, Ba, Mg)$_{10}$(PO4)$_6$C$_{12}$ (hereinafter abbreviated as SCA), and has a light emission spectrum and an excitation spectrum shown in FIG. 11. A peak wavelength of the light emission spectrum is 448 nm. As obvious from the excitation spectrum, the third fluorescent material 33 is excited and generates light in response to both the first excitation light having the central wavelength of 415 nm emitted from the first laser diode 4 and the third excitation light having the central wavelength of 375 nm emitted from the third laser diode 30. The rate of excitation and light generation attributed to the first excitation light having the central wavelength of 415 nm is about 50% of the rate of excitation and light generation attributed to the third excitation light having the central wavelength of 375 nm. The third fluorescent material 33 hardly generates light in response to the second excitation light having the central wavelength of 445 nm emitted from the second laser diode 5.

Next, the operation of the apparatus having the above configuration is described.

[When the Subject Q is Observed in the Special Light Observation Mode]

In the special light observation mode, the light source control unit 7 lights the first laser diode 4 alone. The first excitation light emitted from the first laser diode 4 is guided to the wavelength converting unit 12 of the light source device 2 through the first optical fiber 8, the optical coupler 32, and the third optical fiber 11 as described above. The wavelength converting unit 12 converts the wavelength of the first excitation light that has entered, and emits the light as the illumination light P1 for special light to apply the illumination light P1 for special light to the subject Q.

The imaging section 20 images the reflected light F when the illumination light P1 is applied to the subject Q, and the imaging section 20 outputs an image signal acquired by this imaging.

The image signal output from the imaging section 20 is input to the image processing section 21, and the image processing section 21 performs signal processing to allocate the light receiving signal of the blue pixel to the light receiving signals of the blue and green pixels from the image signal and allocate the light receiving signal of the green pixel to the light receiving signal of the red pixel. The image processing section 21 subjects the processed signal to preset image processing, and generates a special light observation image in which the capillary vessel K in the surface layer of the mucous membrane has an approximately brown color and the thick blood vessel K in the deep part has an approximately blue-green color.

The image display section 22 performs processing to display the special light observation image generated by the image processing section 21 on the monitor in accordance with the special light observation mode, and displays, on the monitor, the special light observation image with enhanced contrast in which, for example, the capillary vessel K in the surface layer of the mucous membrane is brown and the thick blood vessel K in the deep part is blue-green, as described above.

The observation of the subject Q in the special light observation mode is substantially similar to that in the first embodiment described above. However, the spectrum of the illumination light P1 is slightly changed by the addition of the third fluorescent material 33.

Figure 12:
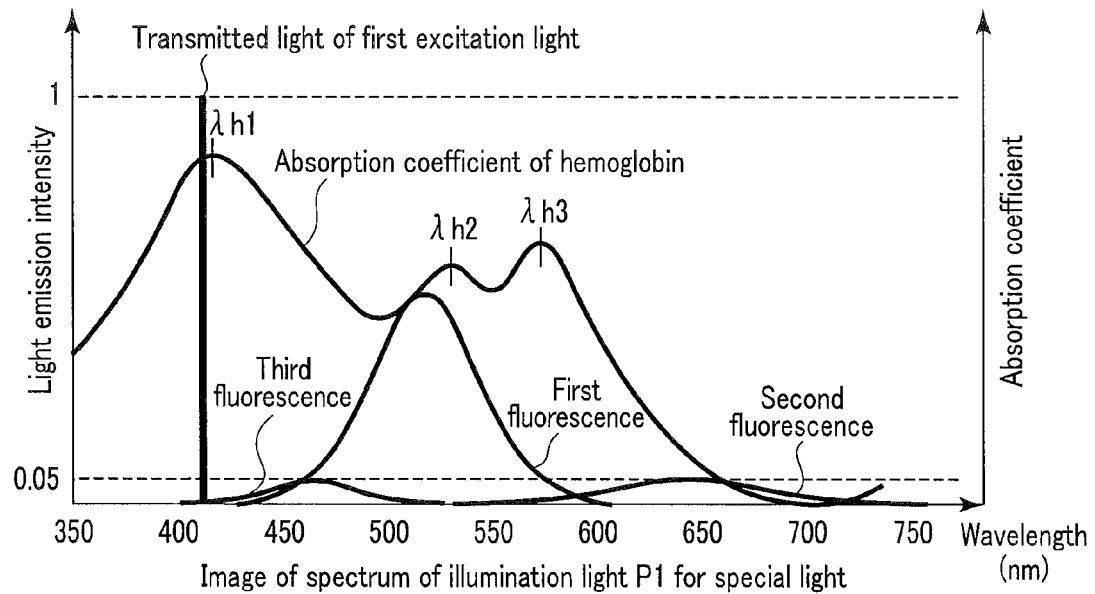
FIG. 12 is a graph showing a spectrum of illumination light in a special light observation mode in the same apparatus.

FIG. 12 shows an image graph of the spectrum of the illumination light P1 in the special light observation mode. The illumination light P1 is light which is the mixture of the first fluorescence, the second fluorescence, the third fluorescence, and the first excitation light which has not been absorbed by and has passed through the first fluorescent material 17. The spectrum of the illumination light P1 is a spectrum which is the mixture of the spectrum of the first fluorescence, the spectrum of the second fluorescence, the spectrum of the third fluorescence, and the spectrum of the first excitation light.

In the present embodiment, the thickness and concentration of the third fluorescent material 33 are also set so for the third fluorescence that the spectral intensity of the third fluorescence is less than or equal to one twentieth of the intensity of the transmitted light of the first excitation light which is the maximum intensity of the illumination light P1 for special light. It is particularly preferable that the third fluorescent material 33 is hardly excited by the first excitation light.

Thus, in the illumination light P1 for special light, there are wavelength lacking regions in the region (region having a wavelength longer than about 580 nm) having a wavelength longer than that of the spectrum of the first fluorescence and in the region (around 420 nm to around 480 nm) between the spectrum of the transmitted light of the first excitation light and the spectrum of the first fluorescence, respectively, as in the first embodiment described above.

Therefore, as in the first embodiment described above, when the surface layer of the mucous membrane of the subject Q is observed in the special light observation mode, the transmitted light of the first excitation light having the wavelength of about 415 nm is strongly absorbed by the hemoglobin in the capillary vessel K in the surface layer of the mucous membrane and strongly reflected and scattered in the part of the surface layer of the mucous membrane where the blood vessel K is not present.

In contrast, the first fluorescence having the wavelength of about 520 nm penetrates the mucous membrane deeper than the transmitted light of the first excitation light, and is then scattered and reflected, and absorbed by the hemoglobin in the thick blood vessel K in the deep part.

As a result, the image display section 22 displays, on the monitor, the special light observation image with enhanced contrast in which, for example, the capillary vessel K in the surface layer of the mucous membrane is brown and the thick blood vessel K in the deep part is blue-green, as described above.

[When the Mode is Switched from the Special Light Observation Mode to the Normal Light Observation Mode to Observe the Subject Q]

In the normal light observation mode, the light source control unit 7 lights the second laser diode 5 and the third laser diode 30 in addition to the first laser diode 4 which is being lighted, leading to a so-called three-light simultaneous lighting state.

Figure 13:
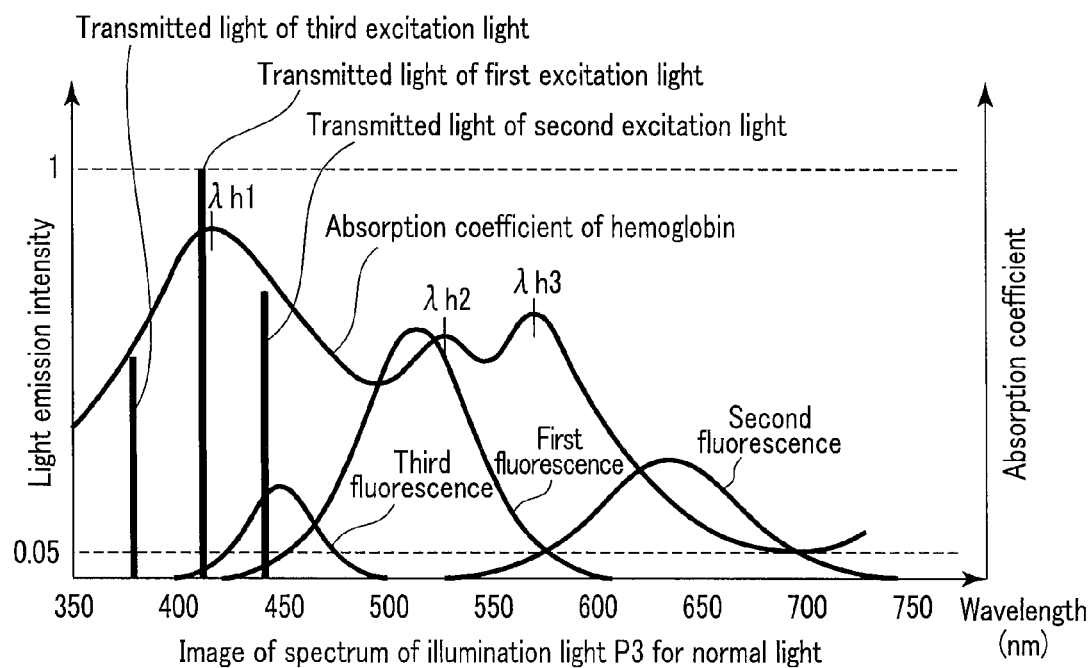
FIG. 13 is a graph showing a spectrum of illumination light in a normal light observation mode in the same apparatus.

FIG. 13 is a graph showing a spectrum of the illumination light P3 in the normal light observation mode. The illumination light P3 for normal light is the addition of the second fluorescence, the second excitation light which has not been absorbed by and has passed through the second fluorescent material 18, the third fluorescence, and the third excitation light which has not been absorbed by and has passed through the third fluorescent material 33 to the illumination light P1 in the special light observation mode.

The spectrum of the illumination light P3 for normal light is a spectrum in which the spectrum of the second excitation light, the spectrum of the second fluorescence, the spectrum of the third excitation light, and the spectrum of the third fluorescence are added to the spectrum of the illumination light P1 for special light.

In the illumination light P3 for normal light, the spectrum of the second excitation light having the central wavelength of 445 nm and the spectrum of the third fluorescence having the peak wavelength of 448 nm are added to the wavelength lacking region (around 420 nm to around 480 nm) between the spectrum of the first excitation light and the spectrum of the first fluorescence which is the wavelength lacking region in the illumination light P1 for special light. Moreover, the spectrum of the second fluorescence having a peak wavelength of about 650 nm is added to the wavelength lacking region (around 580 nm and over) on the longer wavelength side than the spectrum of the first fluorescence.

The illumination light P3 in the normal light observation mode obtains the white light by adding a spectrum to the wavelength lacking region of the illumination light P1 for special light. The second excitation light and the third excitation light also excite the first fluorescent material 17.

However, the light amounts of the first and second excitation light are adjusted so that the illumination light P3 will be the white light.

Thus, the spectra of the second and third fluorescences are added to the wavelength lacking region (around 420 nm to around 480 nm) between the spectrum of the first excitation light and the spectrum of the first fluorescence which is the wavelength lacking region in the illumination light P1 for special light, and the spectrum of the second fluorescence is added to the wavelength lacking region (around 580 nm and over) on the longer wavelength side than the spectrum of the first fluorescence, so that the illumination light (white light) P3 for normal light is obtained.

Thus, according to the second embodiment described above, the third laser diode 30 is added to the first embodiment described above, and the third fluorescent material 33 is added to the first and second fluorescent materials 17 and 18. In the special light observation mode, the light source control unit 7 lights the first laser diode 4 alone to emit the illumination light P1. In the normal light observation mode, the light source control unit 7 simultaneously lights the first, second, and third laser diodes 4, 5, and 30 to emit the illumination light P3 for normal light. Consequently, in the special light observation mode, it is possible to display the special light observation image with enhanced contrast in which, for example, the capillary vessel K in the surface layer of the mucous membrane is brown and the thick blood vessel K in the deep part is blue-green as in the first embodiment described above. In the normal light observation mode, the capillary vessel K in the surface layer of the mucous membrane is easily observed.

In the illumination light P3 for normal light, the third fluorescence is added to the wavelength region between the spectrum of the first excitation light and the spectrum of the first fluorescence, so that the wavelength lacking region is reduced, and the color rendering properties of the white light of the illumination light P3 can be improved compared to the first embodiment described above.

The third excitation light is light outside the visible light region having a central wavelength of 375 nm, so that the color of the illumination light P3 for normal light is not changed by the third excitation light. Thus, the color of the illumination light P3 is easily adjusted by the third fluorescence.

The third excitation light emitted from the third laser diode 30 is not limited to the central wavelength of 375 nm, and has only to be light which can excite the third fluorescent material 33 and which has a spectrum in a near-ultraviolet wavelength region.

The third fluorescent material 33 is not limited to Eu-activated SCA, and has only to be a material which generates light by the third excitation light and which has a light emission spectrum in the wavelength lacking region between the spectrum of the first fluorescence and the spectrum of the first excitation light. However, it is preferable that the third fluorescent material 33 is hardly excited by the first excitation light.

[Third Embodiment]

Next, a third embodiment of the present invention is described with reference to the drawings. The configuration according to the present embodiment is substantially the same as that according to the previous second embodiment shown in FIG. 9, and the differences are described with reference to FIG. 9.

The present embodiment is different from the previous second embodiment in the third fluorescent material 33 and the light source control unit 7.

The third fluorescent material 33 is excited by the third excitation light having the central wavelength of 375 nm emitted from the third laser diode 30, and includes a peak of a light emission spectrum in the vicinity of a wavelength of 580 nm. It is particularly preferable that the third fluorescent material 33 is hardly excited by the second excitation light having the central wavelength of 445 nm emitted from the second laser diode 5.

If the special light observation mode is input from the input unit 6, the light source control unit 7 simultaneously lights the first laser diode 4 and the third laser diode 30, and emits illumination light P4 for special light from the light source device 2 by the simultaneous lighting.

If the normal light observation mode is input from the input unit 6, the light source control unit 7 simultaneously lights the first laser diode 4, the second laser diode 5, and the third laser diode 30, and emits the illumination light P3 for normal light from the light source device 2 by the simultaneous lighting.

Next, the operation of the apparatus having the above configuration is described.

[When the Subject Q is Observed in the Special Light Observation Mode]

In the special light observation mode, the light source control unit 7 simultaneously lights the first laser diode 4 and the third laser diode 30. The first excitation light emitted from the first laser diode 4 is guided to the optical coupler 32 through the first optical fiber 8 as described above. In addition, the third excitation light emitted from the third laser diode 30 is also guided to the optical coupler 32 through the fourth optical fiber 31. The optical coupler 32 multiplexes the first excitation light guided by the first optical fiber 8 and the third excitation light guided by the fourth optical fiber 31, and guides the multiplexed excitation light to the third optical fiber 11. The multiplexed excitation light is guided to the wavelength converting unit 12 through the third optical fiber 11. The wavelength converting unit 12 converts the wavelength of the multiplexed excitation light that has entered, and emits the light as the illumination light P4 for special light to apply the illumination light P4 for special light to the subject Q.

Figure 14:
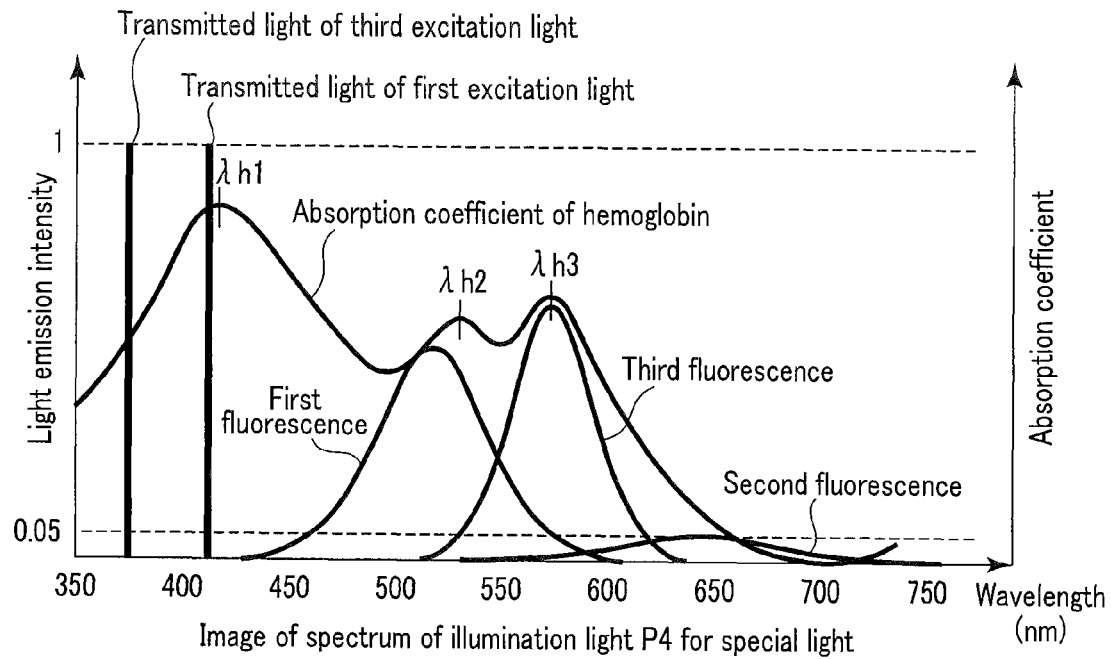
FIG. 14 is a graph showing a spectrum of illumination light in a special light observation mode in a third embodiment of a subject observation apparatus including a light source device according to the present invention.

FIG. 14 shows a spectrum of the illumination light P4 in the special light observation mode. The illumination light P4 is light which is the mixture of the first fluorescence, the second fluorescence, the third fluorescence, the first excitation light which has not been absorbed by and has passed through the first fluorescent material 17, and the third excitation light which has not been absorbed by and has passed through the third fluorescent material 33. The spectrum of the illumination light P4 is a spectrum which is the mixture of the spectrum of the first fluorescence, the spectrum of the second fluorescence, the spectrum of the third fluorescence, the spectrum of the first excitation light, and the spectrum of the third excitation light. The spectrum of the third fluorescence exists in the vicinity of the intensity peak (λh3) of the light absorption spectrum of hemoglobin.

In the illumination light P4 for special light according to the present embodiment, there is a wavelength lacking region in the region having a wavelength longer than that of the spectrum of the third fluorescence, and there is also a wavelength lacking region in the region (around 420 nm to around 480 nm) between the spectrum of the transmitted light of the first excitation light and the spectrum of the first fluorescence.

The imaging section 20 images the reflected light F when the illumination light P4 is applied to the subject Q, and the imaging section 20 outputs an image signal acquired by this imaging. The image processing section 21 subjects the image signal output from the imaging section 20 to image processing, and generates the special light observation image in which the capillary vessel K in the surface layer of the mucous membrane has an approximately brown color and the thick blood vessel K in the deep part has an approximately blue-green color, as described above. The image display section 22 performs processing to display the special light observation image generated by the image processing section 21 on the monitor in accordance with the special light observation mode, and displays, on the monitor, the special light observation image with enhanced contrast in which, for example, the capillary vessel K in the surface layer of the mucous membrane is brown and the thick blood vessel K in the deep part is blue-green, as described above.

[When the Mode is Switched from the Special Light Observation Mode to the Normal Light Observation Mode to Observe the Subject Q]

In the normal light observation mode, the light source control unit 7 simultaneously lights the first laser diode 4, the second laser diode 5, and the third laser diode 30, and emits the illumination light P3 (white light) for normal light from the light source device 2 by the simultaneous lighting.

Figure 15:
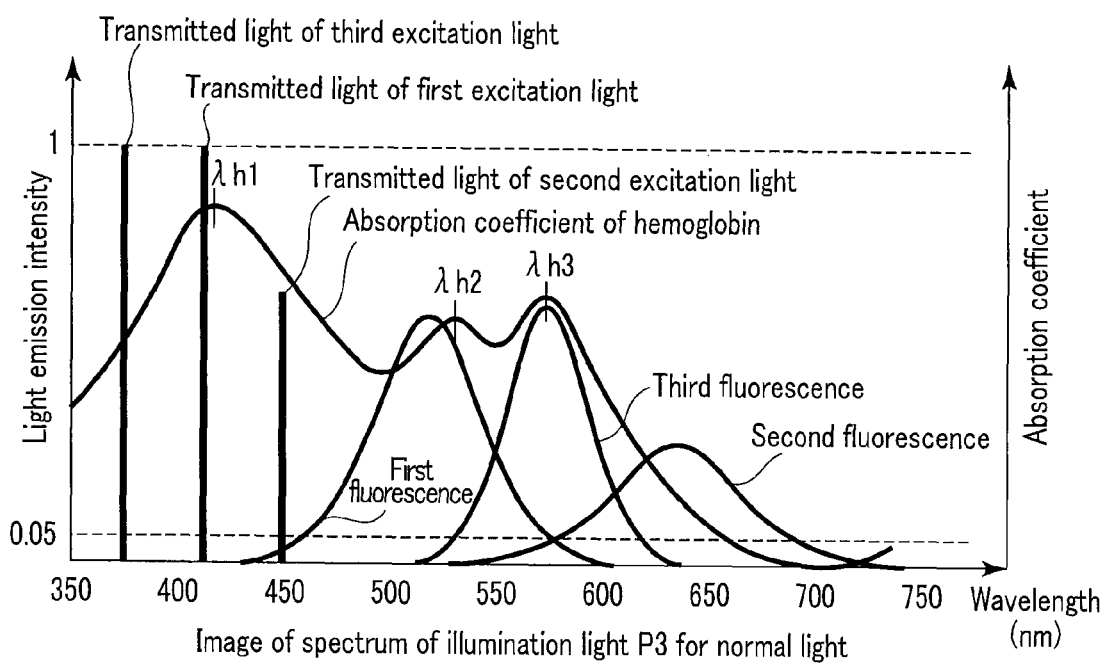
FIG. 15 is a graph showing a spectrum of an illumination light in a normal light observation mode in the same apparatus.

FIG. 15 shows a spectrum of the illumination light P3 in the normal light observation mode. The illumination light P3 is light in which the second fluorescence and the second excitation light which has not been absorbed by and has passed through the second fluorescent material 18 is added to the illumination light P1 in the special light observation mode. The spectrum of the illumination light P3 for normal light is a spectrum in which the spectrum of the second excitation light and the spectrum of the second fluorescence are added to the spectrum of the illumination light P1 for special light.

Therefore, the illumination light P3 in the normal light observation mode obtains the white light by adding the second fluorescence and the second excitation light which has not been absorbed by and has passed through the second fluorescent material 18 to the wavelength lacking region of the illumination light P1 in the special light observation mode, that is, the region having a wavelength longer than that of the spectrum of the third fluorescence, and to the wavelength lacking region (around 420 nm to around 480 nm) between the spectrum of the transmitted light of the first excitation light and the spectrum of the first fluorescence.

Thus, according to the third embodiment described above, the third fluorescent material 33 which is excited by the third excitation light having the central wavelength of 375 nm emitted from the third laser diode 30 and which has a peak of a light emission spectrum in the vicinity of the wavelength of 580 nm is provided. In the special light observation mode, the first laser diode 4 and the third laser diode 30 are simultaneously lighted to emit the illumination light P4. In the normal light observation mode, the first laser diode 4, the second laser diode 5, and the third laser diode 30 are simultaneously lighted to emit the illumination light P3. Consequently, in the illumination light P1 for special light, the spectrum of the third fluorescence exists in the vicinity of the intensity peak ($\lambda h3$) of the light absorption spectrum of hemoglobin, so that it is possible to display, on the monitor, the special light observation image with enhanced contrast in which, for example, the capillary vessel K in the surface layer of the mucous membrane is brown and the thick blood vessel K in the deep part is blue-green.

In the illumination light P2 for normal light, the third fluorescence is added to the wavelength region having low spectral intensity between the spectrum of the first fluorescence and the spectrum of the second fluorescence, so that the color rendering properties of the white light of the illumination light P2 can be improved compared to that of the white light of the illumination light P2 according to the first embodiment described above.

[Fourth Embodiment]

Next, a fourth embodiment of the present invention is described with reference to the drawings. The configuration according to the present embodiment is substantially the same as that according to the previous second embodiment shown in FIG. 9, and the differences are described with reference to FIG. 9.

The present embodiment is different from the previous second embodiment in that the third laser diode 30, the third fluorescent material 33, and a second special light observation mode are added.

In the first to third embodiments, the hemoglobin in the blood vessel K is highlighted and observed as the observation target in the special light observation mode.

In contrast, according to the present embodiment, the second special light observation mode different from the previously described special light observation mode is added. In the second special light observation mode, substances other than the hemoglobin in the blood vessel K, for example, a drug such as a fluorescent probe administered to the subject Q or cells in the subject Q are observed as the observation target. The previously described special light observation mode is referred to as the first special light observation mode.

The input unit 6 inputs observation mode information indicating one of the normal light observation mode, the first special light observation mode, and the second special light observation mode, and sends this observation mode information to the light source control unit 7.

If the first special light observation mode is input, the light source control unit 7 lights the first laser diode 4 alone, and emits the illumination light P1 for special light from the light source device 2.

If the second special light observation mode is input, the light source control unit 7 lights the third laser diode 30 alone, and emits an illumination light P5 for special light from the light source device 2.

If the normal light observation mode is input, the light source control unit 7 simultaneously lights first and second laser diodes 8 and 10, and emits the illumination light P2 for normal light from the light source device 2.

The illumination light P1 for special light according to the present embodiment is the same as the illumination light P1 for special light according to the first embodiment described above, and the illumination light P2 for normal light is also the same as the illumination light P2 for normal light according to the first embodiment described above.

The peak of the spectrum of one or both of the third excitation light and the third fluorescence is selected to be located in the vicinity of a peak of light absorption of an observation target, for example, a substance including a drug such as a fluorescent probe or cells in the subject Q.

The first fluorescent material 17 and the second fluorescent material 18 hardly generate light in response to the third excitation light. The third fluorescent material 33 hardly generates light in response to the first excitation light and the second excitation light.

The third fluorescent material 33 may generate light in response to the second excitation light. However, in the normal light observation mode, the light amounts of the first excitation light and the second excitation light are adjusted so that the illumination light P2 will be the white light.

Next, the operation of the apparatus having the above configuration is described.

[When the Subject Q is Observed in the First Special Light Observation Mode]

In the first special light observation mode, the light source control unit 7 lights the first laser diode 4 alone, and emits the illumination light P1 for special light from the light source device 2. In the first special light observation mode, as in the first embodiment described above, the reflected light F when the illumination light P1 for special light is applied to the subject Q is imaged, and the image signal acquired by this imaging is subjected to image processing, whereby the special light observation image with enhanced contrast in which, for example, the capillary vessel K in the surface layer of the mucous membrane is brown and the thick blood vessel K in the deep part is blue-green is displayed on the monitor.

[When the Mode is Switched from the First Special Light Observation Mode to the Second Special Light Observation Mode to Observe the Subject Q]

In the second special light observation mode, the light source control unit 7 lights the third laser diode 30 alone, and emits an illumination light P5 for special light from the light source device 2. In the second special light observation mode, the reflected light F when the illumination light P5 for special light is applied to the subject Q is imaged, and the image signal acquired by this imaging is subjected to image processing, whereby an image with enhanced contrast between a substance, for example, a drug such as a fluorescent probe administered to the subject Q or cells in the subject Q which is the observation target and other substances is displayed on the monitor.

In this case, the observation target is enhanced and observed by the difference of characteristics such as light absorption, reflection, and scattering of the observation target, here, the substance including the drug such as the fluorescent probe or cells in the subject Q in response to each light of the third excitation light and the third fluorescence emitted from the third laser diode 30, and characteristics such as light absorption, reflection, and scattering of substances around the observation target.

Thus, according to the fourth embodiment described above, the second special light observation mode is added, and in this second special light observation mode, the third laser diode 30 alone is lighted, and the illumination light P5 is emitted from the light source device 2. Therefore, it is possible to enhance and observe, as the observation target, substances other than the hemoglobin in the blood vessel K, for example, the drug such as the fluorescent probe administered to the subject Q or cells in the subject Q.

According to the fourth embodiment described above, the first and second special light observation modes are switched, so that it is possible to switch and then highlight and observe different kinds of observation targets in one wavelength converting unit 12.

The present invention is not completely limited to the embodiments described above, and modifications of components can be made at the stage of carrying out the invention without departing from the spirit thereof. Further, various inventions can be made by properly combining the components disclosed in the embodiments described above. For example, some of all the components shown in the embodiments described above may be eliminated. Moreover, the components in different embodiments may be properly combined.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A light source device comprising:
   excitation light sources configured to emit a plurality of excitation light including mutually different spectra;
   wavelength converters configured to wavelength-convert the plurality of excitation light emitted from the excitation light sources into light having mutually different spectra and configured to be disposed in a common application region of the plurality of excitation light;
   an input configured to input observation modes including a normal light observation mode and a special light observation mode to highlight a particular observation target; and
   a light source controller configured to switch a combination of the excitation light sources that are lighted among the excitation light sources based on the observation mode input to the input,
   wherein light emitted from the wavelength converter is used as illumination light, and the illumination light corresponding to the observation modes is emitted from a same emitting portion,
   wherein the excitation light sources further comprise an optical coupler configured to couple the plurality of excitation light, and
   wherein the wavelength converters are separated from the excitation light sources by more than a length of the optical coupler.

2. The light source device according to claim 1, wherein the excitation light sources comprise:
   a first excitation light source configured to emit a first excitation light including a first spectrum; and
   a second excitation light source configured to emit a second excitation light including a second spectrum different from the first spectrum, and
   the light source controller is configured to switch between the lighting of the first excitation light source alone and simultaneous lighting of the first and second excitation light sources based on the observation mode input to the input.

3. The light source device according to claim 2, wherein the wavelength converters comprise:
   a first wavelength converter configured to emit light having a third spectrum that is longer in wavelength than the first spectrum and that is different from the second spectrum when the first excitation light is applied; and
   a second wavelength converter configured to emit light having a fourth spectrum that is longer in wavelength than the second spectrum and that is different from the first and third spectra when the second excitation light is applied.

4. The light source device according to claim 3, wherein when the special light observation mode is input to the input, the light source controller lights the first excitation light source alone to emit first illumination light including the first and third spectra, and
   when the normal light observation mode is input to the input, the light source controller simultaneously lights the first and second excitation light sources to emit second illumination light including the first to fourth spectra.

5. The light source device according to claim 4, wherein in a wavelength region located in the vicinity of a peak of light absorption of the particular observation target in a visible light region, the first illumination light has a higher spectral intensity than in a low-light-absorption wavelength region located apart from the peak of the light absorption.

6. The light source device according to claim 5, wherein the particular observation target includes peaks of the light absorption, and
in wavelength regions located in the vicinity of the mutually different peaks of light absorption, the first spectrum and the third spectrum have higher spectral intensities than in low-light-absorption wavelength regions located apart from the peaks of the light absorption.

7. The light source device according to claim 6, wherein the particular observation target is hemoglobin in blood, and
the first and third spectra have higher spectral intensities in wavelength regions of 400 nm to 440 nm and 525 nm to 555 nm, respectively, in the vicinity of the peak of the light absorption of the hemoglobin.

8. The light source device according to claim 5, wherein in the low-light-absorption wavelength regions located apart from the peak of the light absorption of the particular observation target, the first illumination light includes wavelength lacking region in which spectral intensity is less than or equal to a predetermined value compared to the maximum intensity of the light emission spectrum of the first illumination light.

9. The light source device according to claim 8, wherein the wavelength lacking regions are configured so that the spectral intensity is less than or equal to one twentieth of the maximum intensity of the light emission spectrum in the first illumination light.

10. The light source device according to claim 8, wherein the first illumination light includes a first wavelength lacking region in a wavelength region between the first spectrum and the third spectrum.

11. The light source device according to claim 10, wherein the second illumination light includes the second spectrum in the first wavelength lacking region.

12. The light source device according to claim 8, wherein the first illumination light includes a second wavelength lacking region in a wavelength region on the longer wavelength side than the third spectrum.

13. The light source device according to claim 4, wherein the second illumination light is a white light.

14. The light source device according to claim 3, wherein the second wavelength converter hardly wavelength-converts the first excitation light, and includes at least one of transmitting and scattering properties.

15. The light source device according to claim 3, wherein the first wavelength converter is a green fluorescent material having a peak of a light emission spectrum in a wavelength region of 500 nm to 580 nm.

16. The light source device according to claim 3, wherein the second wavelength converter is a red fluorescent material having a peak of a light emission spectrum in a wavelength region of 600 nm to 750 nm.

17. The light source device according to claim 3, wherein the second wavelength converter is a yellow fluorescent material having a peak of a light emission spectrum in a wavelength region of 550 nm to 650 nm.

18. The light source device according to claim 3, further comprising:

a third excitation light source configured to emit third excitation light having a fifth spectrum different from the first to fourth spectra,
wherein the wavelength converters further comprises a third wavelength converter configured to emit light having a sixth spectrum that is longer in wavelength than the fifth spectrum and that is different from the first to fourth spectra when the third excitation light is applied.

19. The light source device according to claim 18, wherein
when the special light observation mode is input to the input, the light source controller lights the first excitation light source alone to emit first illumination light including the first and third spectra, and
when the normal light observation mode is input to the input, the light source controller simultaneously lights the third excitation light source in addition to the first and second excitation light sources to emit second illumination light including the first to sixth spectra.

20. The light source device according to claim 19, wherein
the first illumination light includes, in a wavelength region between the first spectrum and the third spectrum, a first wavelength lacking region in which spectral intensity is less than or equal to one twentieth of the maximum intensity of the light emission spectrum of the first illumination light, and
the sixth spectrum in the second illumination light exists in the first wavelength lacking region.

21. The light source device according to claim 18, wherein the fifth spectrum exists in a near-ultraviolet wavelength region.

22. The light source device according to claim 2, wherein the first spectrum exists in a wavelength region of 400 nm to 430 nm.

23. The light source device according to claim 2, wherein the second spectrum exists in a wavelength region of 430 nm to 460 nm.

24. The light source device according to claim 1, wherein the excitation light sources include:
a first excitation light source configured to emit first excitation light including a first spectrum;
a second excitation light source configured to emit second excitation light including a second spectrum different from the first spectrum; and
a third excitation light source configured to emit third excitation light having a fifth spectrum different from the first and second spectra,
the wavelength converters comprise:
a first wavelength converter configured to emit light having a third spectrum that is longer in wavelength than the first spectrum and that is different from the second to fifth spectra when the first excitation light is applied;
a second wavelength converter configured to emit light having a fourth spectrum that is longer in wavelength than the second spectrum and that is different from the first, third, and fifth spectra when the second excitation light is applied; and
a third wavelength converter configured to emit light having a sixth spectrum that is longer in wavelength than the fifth spectrum and that is different from the first to fourth spectra when the third excitation light is applied, and
the light source controller is configured to switch a combination of the excitation light sources that are lighted among the first to third excitation light sources based on the observation mode input to the input.

25. The light source device according to claim 24, wherein
when the special light observation mode is input to the input, the light source controller simultaneously lights the first and third second excitation light sources to emit first illumination light including the first, third, fifth, and sixth spectra, and
when the normal light observation mode is input to the input, the light source controller simultaneously lights the first to third excitation light sources to emit second illumination light including the first to sixth spectra.

26. The light source device according to claim 25, wherein in wavelength regions located in the vicinity of different peaks among peaks of light absorption of the particular observation target in a visible light region, the first, third, and sixth spectra have higher spectral intensities than in low-light-absorption wavelength regions located apart from the peaks of the light absorption, respectively.

27. The light source device according to claim 24, wherein
the input is configured to input a normal light observation mode, a first special light observation mode to highlight a first particular observation target, and a second special light observation mode to highlight a second particular observation target different from the first particular observation target,
when the first special light observation mode is input to the input, the light source controller lights the first excitation light source alone to emit first illumination light including the first and third spectra,
when the normal light observation mode is input to the input, the light source controller simultaneously lights the first and second excitation light sources to emit second illumination light including the first to fourth spectra, and
when the second special light observation mode is input to the input, the light source controller lights the third excitation light source alone to emit third illumination light including the fifth and sixth spectra.

28. The light source device according to claim 27, wherein in a wavelength region located in the vicinity of a peak of light absorption of the second particular observation target, the third illumination light has a higher spectral intensity than in a low-light-absorption wavelength region located apart from the peak of the light absorption of the second particular observation target.

29. A subject observation apparatus comprising:
the light source device according to claim 1, the illumination light emitted from the light source device being applied to a subject; and
an image acquiring unit configured to acquire image information regarding the subject.

30. A light source control method comprising:
inputting one of observation modes including a normal light observation mode and a special light observation mode to highlight a particular observation target;
switching a combination of excitation light sources that are lighted among excitation light sources based on the input observation mode information;
emitting excitation light having mutually different spectra from the lighted excitation light sources and then applying the excitation light to wavelength converters; and
using light emitted from the wavelength converters as illumination light, and emitting the illumination light corresponding to the observation modes from a same emitting portion,
wherein the excitation light sources further comprise an optical coupler configured to couple the plurality of excitation light, and
wherein the wavelength converters are separated from the excitation light sources by more than a length of the optical coupler.

31. The light source control method according to claim 30, wherein
the excitation light sources comprise:
a first excitation light source configured to emit first excitation light including a first spectrum; and
a second excitation light source configured to emit second excitation light including a second spectrum different from the first spectrum,
the light source controller is configured to switch between the lighting of the first excitation light source alone and simultaneous lighting of the first and second excitation light sources based on the observation mode input to the input,
the wavelength converters comprise:
a first wavelength converter configured to emit light having a third spectrum that is longer in wavelength than the first spectrum and that is different from the second spectrum when the first excitation light is applied; and
a second wavelength converter configured to emit light having a fourth spectrum that is longer in wavelength than the second spectrum and that is different from the first and third spectra when the second excitation light is applied,
in the special light observation mode, the first excitation light source alone is lighted to emit first illumination light including the first and third spectra from the wavelength converters, and
in the normal light observation mode, the first and second excitation light sources are simultaneously lighted to emit second illumination light including the first to fourth spectra from the wavelength converters.

32. The light source control method according to claim 31, wherein
the excitation light sources further includes a third excitation light source configured to emit third excitation light having a fifth spectrum different from the first to fourth spectra,
the wavelength converters further comprise a third wavelength converter configured to emit light having a sixth spectrum that is longer in wavelength than the fifth spectrum and that is different from the first to fourth spectra when the third excitation light is applied, and
in a second special light observation mode to highlight a second particular observation target different from the particular observation target, the third excitation light source alone is lighted to emit third illumination light including the fifth and sixth spectra.

* * * * *